United States Patent
Ouyang et al.

(10) Patent No.: US 9,649,014 B2
(45) Date of Patent: May 16, 2017

(54) SINGLE USE MEDICAL DEVICES

(75) Inventors: Xiaolong Ouyang, Palo Alto, CA (US); Avram Allan Edidin, Portola Valley, CA (US); Hui Tian, Cupertino, CA (US)

(73) Assignees: Xiaolong Ouyang, Bellevue, WA (US); Avram Allan Edidin, Portola Valley, CA (US)

( * ) Notice: Subject to any disclaimer, the term of this patent is extended or adjusted under 35 U.S.C. 154(b) by 1011 days.

(21) Appl. No.: 13/094,415

(22) Filed: Apr. 26, 2011

(65) Prior Publication Data

US 2011/0270179 A1 Nov. 3, 2011

Related U.S. Application Data

(60) Provisional application No. 61/328,955, filed on Apr. 28, 2010, provisional application No. 61/330,954, filed on May 4, 2010.

(51) Int. Cl.
*A61M 5/50* (2006.01)
*A61B 1/00* (2006.01)

(52) U.S. Cl.
CPC ...... *A61B 1/00062* (2013.01); *A61B 1/00124* (2013.01)

(58) Field of Classification Search
CPC .............. G11C 29/822; G11C 2216/26; A61B 1/00071; A61B 1/00103; A61B 1/00108; A61B 1/05; A61B 1/00062; A61B 1/00124
USPC ............ 604/110; 348/231.99, 222.1, E5.024, 348/E5.031; 327/525; 326/6; 396/16–17
See application file for complete search history.

(56) References Cited

U.S. PATENT DOCUMENTS

| | | | | |
|---|---|---|---|---|
| 5,010,876 A * | 4/1991 | Henley et al. | ................ | 600/112 |
| 5,666,561 A * | 9/1997 | Stephenson, III | ..... | G03B 17/55 |
| | | | | 396/284 |
| 6,507,699 B2 * | 1/2003 | Lemoine | ................ | G03B 19/04 |
| | | | | 396/287 |
| 6,518,823 B1 * | 2/2003 | Kawai | ........................ | 327/525 |
| 6,917,380 B1 * | 7/2005 | Tay | ............................... | 348/247 |
| 7,256,446 B2 * | 8/2007 | Hu | ........................ | G11C 17/16 |
| | | | | 257/316 |
| 7,428,378 B1 * | 9/2008 | | | Warpakowski |
| | | Furlan | ..................... | G03B 7/16 |
| | | | | 348/370 |
| 2003/0151680 A1 * | 8/2003 | McDermott | ........... | H04N 5/335 |
| | | | | 348/231.6 |
| 2004/0138558 A1 * | 7/2004 | Dunki-Jacobs | ........ | A61B 1/041 |
| | | | | 600/431 |
| 2006/0152601 A1 * | 7/2006 | Parekh | .................... | H04N 5/335 |
| | | | | 348/231.99 |
| 2007/0081920 A1 * | 4/2007 | Murphy | ............. | G01N 21/8483 |
| | | | | 422/400 |
| 2007/0210162 A1 * | 9/2007 | Keen | .................... | G06K 19/073 |
| | | | | 235/451 |
| 2008/0004642 A1 * | 1/2008 | Birk et al. | .................... | 606/157 |

(Continued)

*Primary Examiner* — Quynh-Nhu H Vu
(74) *Attorney, Agent, or Firm* — Maschoff Brennan

(57) ABSTRACT

A single use medical device can include a single use medical device module configured for use within a body of a subject receiving a medical procedure. It can also include an electronic component having a one-time programmable ("OTP") component that is configured to render the single use medical device module unusable after being used in the medical procedure in the subject.

23 Claims, 14 Drawing Sheets

OTP Content may be 1 bit or multiple bits

CID - Case ID
TS - Time Stamp
DB - Disabling Bit

(56) References Cited

U.S. PATENT DOCUMENTS

| | | | |
|---|---|---|---|
| 2008/0097550 A1* | 4/2008 | Dicks .................. | A61B 5/0022 607/59 |
| 2009/0227897 A1* | 9/2009 | Wendt et al. ................. | 600/583 |
| 2009/0287663 A1* | 11/2009 | Takeuchi .......................... | 707/3 |
| 2011/0037876 A1* | 2/2011 | Talbert et al. ........... | 348/231.99 |

* cited by examiner

SINGLE USE MEDICAL DEVICES

CROSS-REFERENCE TO RELATED PATENT APPLICATIONS

This patent application claims benefit of provisional patent applications U.S. Ser. No. 61/328,955, filed Apr. 28, 2010, and U.S. Ser. No. 61/330,954, filed May 4, 2010, which provisional patent applications are incorporated herein by specific reference in their entirety.

BACKGROUND

The term "single-use" in medical device means that a device or component is disposed after single usage on a patient. Single-use methods offer critical benefit for patient and also healthcare providers by eliminating the burden of reprocessing single-use devices ("SUD") and reducing the risk of infection from potential contaminations. With advances of technology and materials, SUDs are becoming practical both economically and logistically.

Single-use devices and methods can benefit patients and healthcare providers by eliminating the burden of reprocessing SUDs and reducing the risk of infection. Particularly, multi-use devices become contaminated with each use and are typically subjected to a sterilization procedure after each use to eliminate the contamination. Sterilization procedures can be burdensome and are not always 100% effective. Any contaminant remaining on the multiuse device after the sterilization procedure can potentially cause an infection in a patient on whom the multi-use device is subsequently used. In comparison, SUDs are only used during a single procedure on a single patient and thus generally do not get exposed to contamination during prior usage.

On the other hand, since SUDs are not re-used, the cost of a single-use device cannot be spread across multiple patients. However, recent advances in technology and materials have made SUDs an economically and logistically practical alternative to multi-use medical devices.

SUMMARY

On one embodiment, a single use medical device can include a single use medical device module configured for use within a body of a subject receiving a medical procedure. The single use medical device module can include an electronic component having a one-time programmable ("OTP") component that is configured to render the single use medical device module unusable after being used in the medical procedure in the subject. Optionally, the electronic component includes an image sensor, such as a CMOS sensor.

In one aspect, the OTP component is operably coupled with the electronic component. In an alternative aspect, the OTP component is embedded in another electronic component.

In one embodiment, the OTP component is configured to operate one time, and thereafter it does not allow the single use medical device to operate.

In one embodiment, the system includes a self-sacrificing module (SSM) that self-destructs after being used one time.

In one embodiment, the OTP component is operably coupled with a timer and an AND circuit, when the timer reaches a certain time, the single use medical device no longer works.

In one embodiment, the OTP component includes a disabling bit (DB) circuit that is programmed to disable the single use medical device when a Clock_out signal is received by the CMOC chip. The DB bit can include circuit logic within the OTP chip that can disable the Clock_in signal.

In one embodiment, the OTP component is configured to control various electronic components of the medical device within the single use medical device module.

In one embodiment, the OTP component is configured to be programmed one time by various electronic components of the medical device within the single use medical device module.

In one embodiment, the OTP component is configured such that a state change of a signal to the OTP component disables the single use medical device module.

In one embodiment, the single use medical device can include or be operably coupled with a controller configured to program the OTP with data, such as a system time stamp and an ID generated from Patient ID. The controller can be configured to read the serial number of one or more electronics modules of the single use medical device module. The controller can be configured to tag a serial number of one or more electronics modules of the single use medical device module, and associate the serial number with a Patient ID.

In one embodiment, the electronic component having the OTP component includes an algorithm that is processed in order to render the single use medical device module unusable after being used in the medical procedure in the subject. The algorithm can be configured to process data in order to detect and/or determine if the OTP component has been programmed.

The single use medical device module can be configured to disable an image sensor by one or more of the following: disabling a clock (CLK) to a chip of the image sensor, the chip being operably coupled with the OTP component; disabling a digital enabling D_en inside the image sensor; or changing a state of the OTP component with "self-destroy" codes.

In one embodiment, a medical device can include a reusable portion, and a single use portion. The single use portion can include the single use module. The medical device can include a reusable portion and a single use portion, with the reusable portion removably receiving the single use portion. The single use portion can include a single use medical device module configured for use within a body of a subject receiving a medical procedure having an electronic component having a one-time programmable ("OTP") component that is configured to render the single use medical device module unusable after being used in the medical procedure in the subject. The single use medical device can be used in a method: using the single use portion; programming the OTP component; and terminating use of the single use portion. Once used, the single use module is inoperable. The method can further include attempting to reuse the single use portion, the single use portion being unusable. The method can include the single use portion providing an indication that the single use portion has already been used or that the single use portion is not operational.

In one embodiment, a method of use can include: generating a first unique case identifier corresponding to a first unique patient undergoing a medical procedure; obtaining a first time stamp representing a current time; and determining that the OTP component has previously been programmed with a second unique case identifier and a second time stamp, when the first unique case identifier is different than the second unique case identifier, or when the amount of time elapsed from an initial time represented by the second time stamp to a subsequent time represented by the first time stamp is greater than a predetermined amount of time, disabling the single use medical device module by programming a disabling bit on the one-time programmable chip; or determining that the OTP component has not been previously programmed, wherein the single use medical device module is operational.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION

Figure 1:
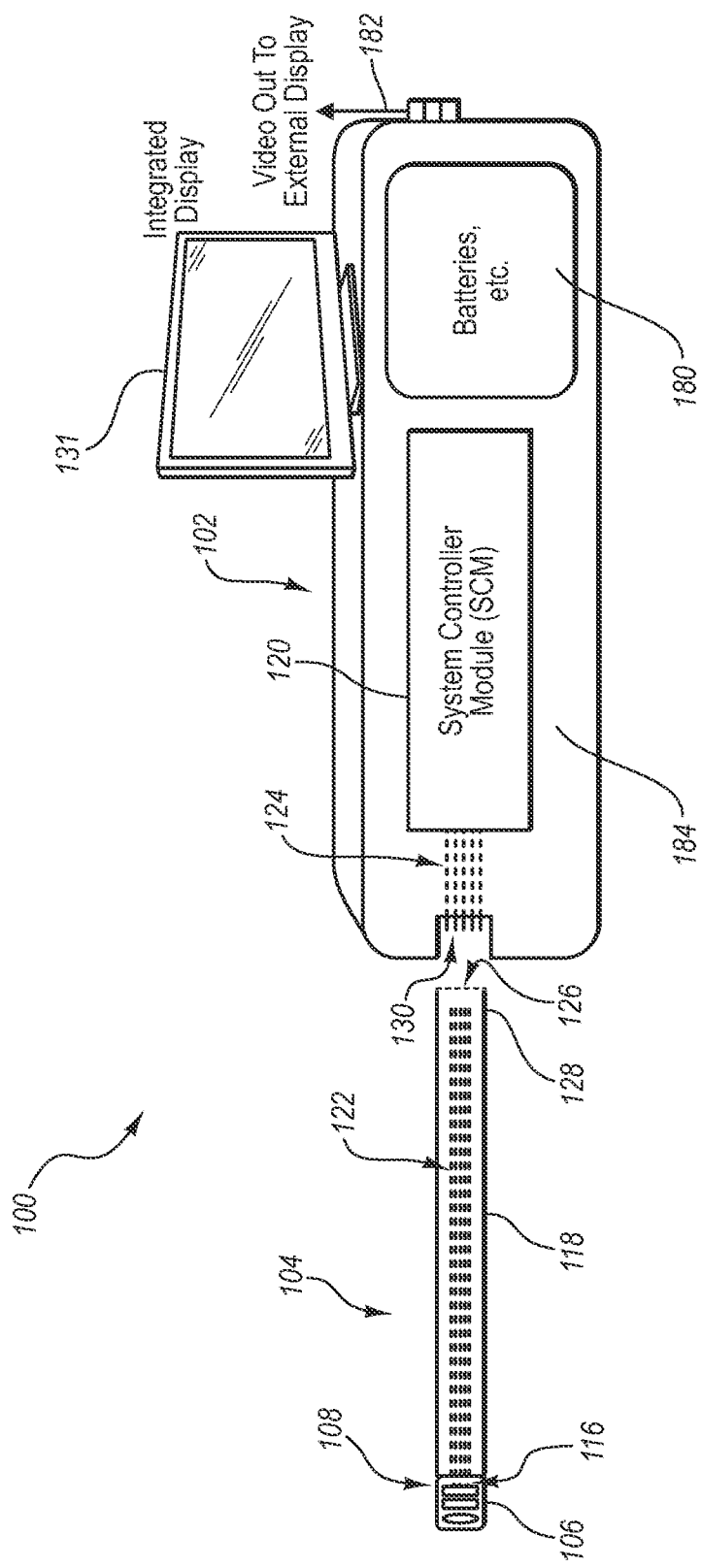
FIG. 1 includes a schematic diagram of an embodiment of a medical device that includes a reusable portion and a single use portion.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present invention is related to single use medical devices that will only work one time. After it is used, the medical device has a single use electronic component that either self-destructs or it renders the medical device unable to be used. The single use electronic component can include hardware and/or software configured to render the medical device unable to be used after it is used. The medical device can be exemplified by an optical endoscope that has the single use electronic components in a disposable portion, such as the portion that is inserted into a patient for an endoscopic procedure. The one time use feature can be located on the disposable portion of the medical device, such as the portion that is inserted within a body.

Generally, the present invention includes a portion that is reusable and one or more portions that are single use. The single use portions are configured to be inoperably after being used one time. The inoperability results in the single use portion being rendered useless.

The single use medical device can include a single use medical device module configured for use within a body of a subject receiving a medical procedure. The single used medical device module can include the feature that disables the single use medical device. The single use medical device module can include an electronic component having a one-time programmable ("OTP") component that is configured to render the single use medical device module unusable after being used in the medical procedure in the subject.

The single use medical device can include a micro image sensor chip such as a complementary metal-oxide-semiconductor ("CMOS") chip having an array of sensor pixels and a plurality of bonding pads disposed along one or more sides or other areas of the CMOS chip. Alternately or additionally, the CMOS chip includes row logic, bias, and/or sample and hold components.

The electronic component can include one or more of the following: a OTP component electronically coupled with a CMOS image sensor, wherein the OTP component only works one time, and thereafter it does not allow the single use medical device to operate; a OTP component located on a CMOS image sensor; a OTP component including a self-sacrificing module (SSM) that self-destructs after being used one time; a OTP component associated with a timer and an AND circuit, when the timer reaches a certain amount of use time, the device no longer works; a OTP component including a disabling bit (DB) circuit that is programmed to disable the single use medical device when a Clock_out signal is received by the DB circuit; and a OTP component controlling various electronic components of the medical device within a disposable portion, and when there is a state change to a single to the OTP component, the disposable portion of the medical device ceases to work.

Accordingly, the present invention generally relates to electronic means for inhibiting multiple uses of single-use devices (SUD), such as single use medical devices. More particularly, some example embodiments relate to electronic means for using hardware, software, and/or mechanical schemes in order to inhibit multiple uses of single-use video probes or endoscopes. This electronic means can include a combination of electronic hardware and firmware to disable the SUDs after single usage with a patient. In particular this invention is applied to single-use video probes or endoscopes having the disabling electronic means on the probe or endoscope portion.

In one embodiment, an endoscope can include a micro image sensor chip on the portion of the endoscope that is inserted within a body of a subject. For example, the micro image sensor chip can be a CMOS chip having an array of sensor pixels and a plurality of bonding pads disposed along one side of the of the CMOS chip. Alternately or additionally, the CMOS chip can include row logic, bias, and sample and hold components. The micro image sensor chip can include an electronic component that disables the micro image sensor chip from functioning once it has been used. As such, the micro image sensor chip can include a self-destructing electronic component.

In one embodiment, a self-destructing electronic component can include an OTP logic or circuitry block component being embedded in the sensor chip. The OTP component can have many different implementations.

In one example, the OTP can include a nonvolatile memory, with bits allocated to store a system Time Stamp (TS) and bits to store an ID such as the Case ID (CID). One bit is used as the Disabling Bit (DB). When the disable bit is "flip" or "burned" the CMOS sensor will be permanently disabled. TS and CID can be programmed one time by the system controller before being permanently disabled.

In one embodiment, a combination of electronic hardware, firmware and/or mechanical means can be included in the disposable portion of a medical device and configured to disable the disposable portion after a single usage for a single patient. For instance, example embodiments can be applied to single-use video probes or endoscopes. More particularly, some embodiments include an endoscope with a micro image sensor chip.

FIG. 1 includes a schematic diagram of an embodiment of a medical device 100 that includes a reusable portion 102 and a single use portion 104. The device 100 of FIG. 1 illustrates an example endoscopic device 100 in which some embodiments can be implemented. The endoscopic device 100 includes a handle 102 and a single use medical device ("SUD") 104 implemented as a disposable catheter 104 or single-use video probe 104.

In some embodiments, the endoscopic device 100 can be configured to be hand-held and/or battery-operated. The endoscopic device can include a self-contained reusable handle 102 that includes electronic components configured for functioning in a medical procedure on its own power, which can include a power source 180, such as rechargeable or disposable batteries. The power source 180 may also be configured to be plugged into a power outlet before and/or during a medical procedure.

The disposable catheter 104 can include a camera and lens assembly 106 disposed on, in or near a distal end 108 of the SUD 104. With combined reference to FIGS. 1 and 2, the camera and lens assembly 108 can include a sensor PCBA 116 that includes a CMOS image sensor 110 mounted on a miniature printed circuit board ("PCB") 112 with one or more additional electronic components. The electronic components can include single use electronic components, such as a one-time programmable ("OTP") chip 114.

Figure 2:
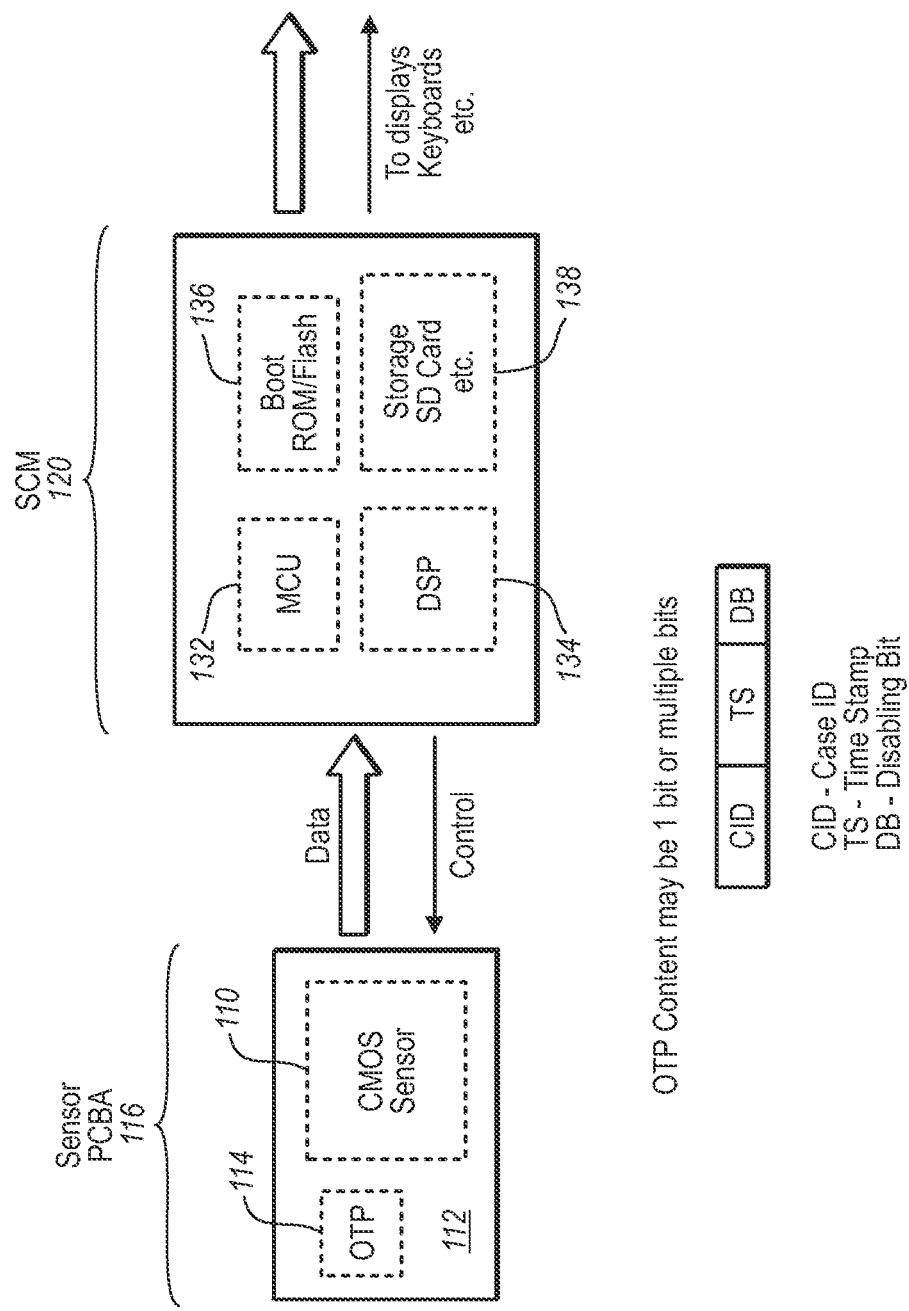
FIG. 2 includes a schematic diagram of an embodiment of electronic components of the medical device of FIG. 1, where the schematic diagram illustrates electronic components in the reusable portion and electronic components in the single use portion.

The PCB 112 with CMOS image sensor 110 and an OTP chip 114 are collectively referred to herein as a sensor PCB assembly ("sensor PCBA") 116. Although the OTP chip 114 is illustrated in FIG. 2 as being included in the PCBA 116 near the CMOS image sensor 110, in other embodiments the OTP chip 114 is included in or near the connector 126 of the disposable catheter 104. In fact, the OTP chip 114 can be located on any portion of the SUD 104.

The OTP chip 114 can have one bit or multiple bits representing, for instance, a time stamp ("TS") indicating a specific time when the disposable catheter 104 is first used, a patient case ID ("CID"), or the like, as indicated at the bottom of FIG. 2. The TS and CID stored in the OTP chip 114 uniquely associate the disposable catheter 104 with a time of first use and a patient. Optionally, a status bit, e.g., a disabling bit, is also included in the content of the OTP chip 114.

In the illustrated embodiment of FIG. 1, the disposable catheter 104 further includes a flexible or rigid tube 118 within which the camera lens assembly 108 is mounted. The camera lens assembly 108 is electrically connected to a system controller module ("SCM") 120 within the handle 102 via electrical lines (e.g., wires, traces, etc.) 122, 124 within the tube 118 and handle 102. Optionally, the disposable catheter 104 includes connector 126 at a proximal end 128 of the tube 118 that is complementary to connector 130 of the handle 102. The connectors 126, 130 collectively provide a mechanical and electrical interface between the disposable catheter 104 and the handle 102. The connectors 126, 130 further provide for easy attachment and detachment of the disposable catheter 104 from the handle 102 in some embodiments.

According to some embodiments, the electrical lines 122, 124 between the sensor PCBA 116 and the SCM provide for a data path and a control path, including power supply (VDD and VSS) to the sensor PCBA 116 and/or LED, clock ("CLK"), single-ended analog output line and/or double-ended differential analog output lines. Optionally, control signals are shared among one or more of electrical lines 122, 124. Optionally, the endoscopic device 100 includes an integrated video display 131. Data representing images obtained by the CMOS image sensor 110 is provided over electrical lines 122, 124 and output to the integrated video display 131. Alternately or additionally, the data representing the images obtained by the CMOS image sensor 110 can have an output 182 configured to be operably coupled to an external video display. It is understood that the integrated video display 131 is not required in all embodiments.

Referring to FIG. 2, in some embodiments, the SCM 120 includes a microcontroller unit ("MCU") 132 or other control module (e.g., controller, microcontroller, processor, microprocessor, or the like), a digital signal processor ("DSP") 134, a Boot read-only memory ("ROM") or flash memory 136, and/or a volatile or non-volatile storage device 138 such as an SD card.

In general, the SCM 120 can write once to the OTP chip 114 and read multiple times from the OTP chip 114. Alternately or additionally, the SCM 120 reads and changes registers on the CMOS image sensor 110 to, for instance, disable the CMOS image sensor 110 by changing its registers.

In operation, at power on or reset, the SCM 120 boots from "boot code" stored in the Boot ROM/Flash 136. In some embodiments, the Boot ROM/Flash 136 also stores firmware for operating the endoscopic device 100 and implementing one or more of the methods described herein. Generally, the content in the Boot ROM/Flash 136 is read-only such that the content cannot be changed or modified by users of the endoscopic device 100.

Accordingly, FIG. 2 provides a schematic diagram of an embodiment of electronic components of the medical device of FIG. 1. The illustrated embodiment is a hand-held battery-operated endoscope device 100 where the camera and lens assembly 106 disposed on, in or near a distal end 108 of the SUD 104. For example, the camera and lens assembly 106 can include a CMOS sensor 110 is mounted on a miniature PCB module 112 (the "SM" module) with some minimal components including passives. The camera module assembly 106 is mounted inside a tube 118 that is flexible or rigid. The camera module assembly 106 is connected to the system controller PCB Module 120 (the "SCM" module) inside the handle 102, through an easy attach and detach interface connector 130, 126. SCM 120 and SM 120 are connected through data path and control path which include power supplies (VDD, VSS) to SM and LED, clock (CLK), single-ended analog output line or double-ended differential analog out lines 122,124. Control signals may be shared among these wires 122, 124.

In some embodiments, the CMOS chip 110 is included within a disposable needle or flexible catheter (the "Catheter") and can be used on a single-use basis. As such, the sterilization process associated with many multiple-use endoscopes and the risk of infection is eliminated. Moreover, the small size of the CMOS chip 110 facilitates truly minimally invasive procedures and real-time images suitable for use with diagnostic and surgical applications according to some embodiments.

In one embodiment, the present invention provides means and methods that are designed to prevent a single-use catheter or SM from being reused or being capable of being reused. In other words, a combination of software and hardware mechanisms can use a CMOS sensor that is disabled after one use and cannot be reused.

Figure 3:
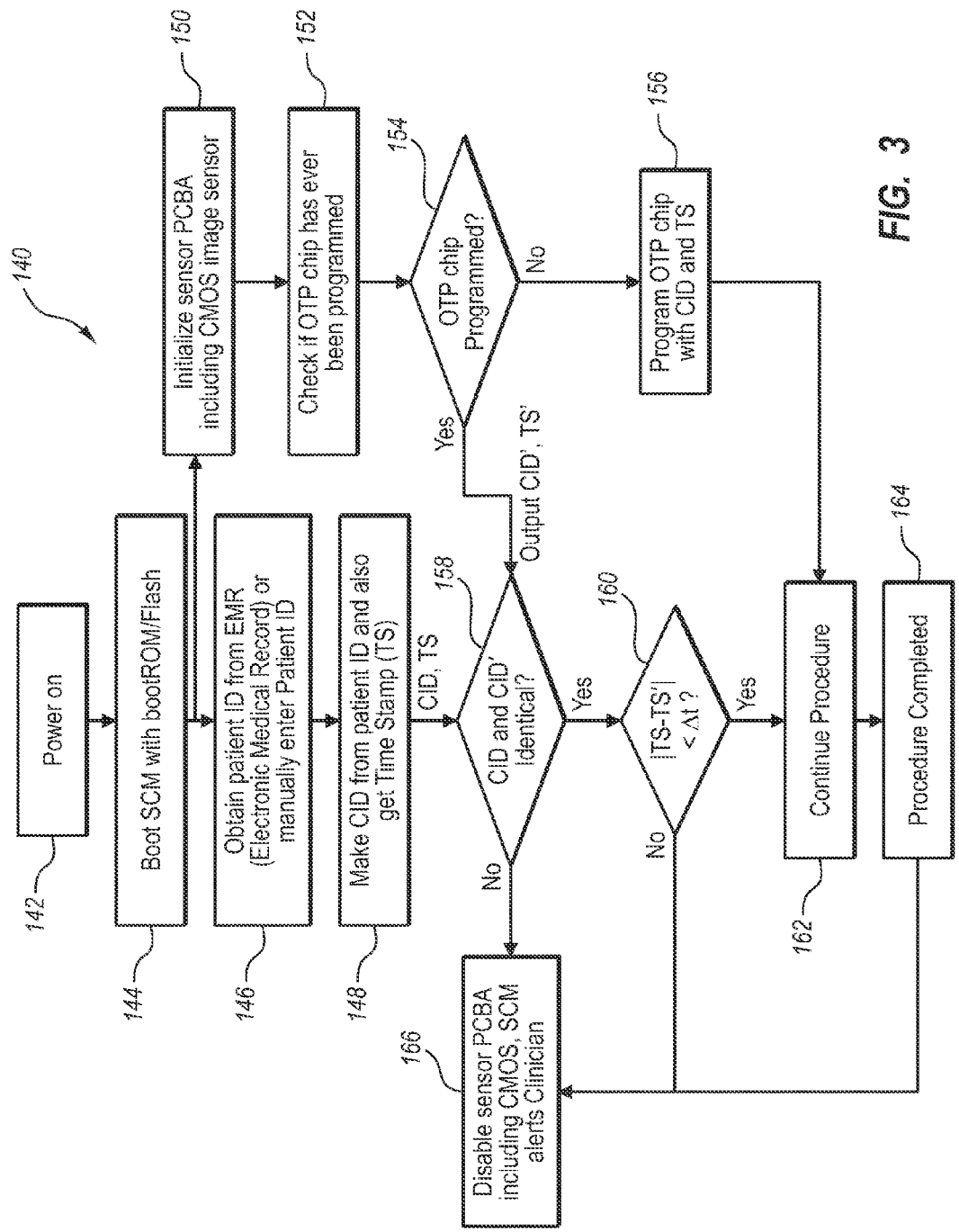
FIG. 3 includes a flow diagram of an embodiment of a process of a single use medical device that inhibits reuse of the single use medical device.

FIG. 3 includes a flow diagram of an embodiment of a process of a single use medical device that inhibits reuse of the single use medical device. FIG. 3 describes the OTP implementation of the components of FIG. 2 in the SUD 104 of FIG. 1. With additional reference to FIG. 3, one example of a method 140 of operating the endoscopic device 100 of FIG. 1 or other devices is disclosed. According to some embodiments, the method 140 generally determines that a component such as a catheter or other medical device component including the sensor PCBA 116 has already been used, and should therefore be disabled, if the OTP chip 114 of the sensor PCBA 116 has been programmed or burned more than a predetermined time (e.g., Δt minutes) prior to checking the OTP chip 114.

In the discussion that follows, the method 140 will be discussed in the context of a disposable catheter 104 including a sensor PCBA 116 that can be implemented with the handle 102, with the understanding that the method 140 can be applied using other components that include sensor PCBAs 116 and/or that are implemented in devices other than the handle 102.

In some embodiments, the method 140 of FIG. 3 begins after a clinician or other healthcare provider opens a sterile package containing a component such as a disposable catheter 104 or other component including a sensor PCBA 116, and snaps the disposable catheter 104 onto the handle 102 via connectors 126, 130. At 142, the handle 102 is powered on or reset, e.g., in response to the clinician pushing a power on/reset button. At step 144, the SCM 120 is booted and initialized from boot ROM/Flash 136. At step 146, a Patient ID is obtained. The Patient ID corresponds to a patient on whom a medical procedure is to be performed using the endoscopic device 100. The Patient ID in some embodiments is obtained in response to the clinician scanning an electronic medical record ("EMR") corresponding to the patient or manually entering the Patient ID using an appropriate input device such as a keyboard connected to the handle 102. At step 148, the SCM 120 automatically generates a Case ID ("CID") corresponding to the Patient ID. The CID is generated according to predefined rules. Alternately or additionally, step 148 further includes obtaining a time stamp ("TS") representing a current time.

In some embodiments, various other steps are executed after or simultaneously with step 144 in association with the sensor PCBA 116. Specifically, at step 150, the SCM 120 initializes the sensor PCBA 116 including the CMOS image sensor 110, and at step 152, the SCM 120 checks the OTP chip 114 to then determine at step 154 whether the OTP chip 114 has ever been programmed. If the OTP chip 114 has never been programmed, indicating that the disposable catheter 104 has never been used, the OTP chip 114 is programmed at step 156 with the CID and TS obtained during step 148. On the other hand, if the SCM 120 determines at step 154 that the OTP chip 114 has previously been programmed, indicating that the disposable catheter 104 has been in use previously, a previously programmed CID' and previously programmed TS' will already be stored in the OTP chip 114 and are output by the OTP chip 114.

At step 158, the SCM 120 determines whether the CID obtained at step 148 is identical to the previously programmed CID' output at step 154. If the CID and CID' are identical at step 158, then the SCM 120 determines at step 160 whether the OTP chip 114 was programmed less than a predetermined Δt minutes prior to checking the OTP chip 114 at step 154. Specifically, in some embodiments, the SCM 120 evaluates at step 160 whether |TS−TS'|<Δt.

If the SCM 120 determines at step 158 that the CID and CID' are identical and if the SCM 120 determines at step 160 that the amount of time elapsed since the OTP chip 114 was first programmed with TS' is less than the predetermined time Δt, the procedure continues at step 162 until completion at step 164. Alternately, if the SCM 120 determines at step 158 that the CID and CID' are not identical, indicating that the patient on whom the disposable catheter 104 is being used is different than a patient on whom the disposable catheter 104 was used previously, or if the SCM 120 determines at step 160 that the amount of time elapsed since the OTP chip 114 was first programmed with TS' is greater than the predetermined time Δt, then at step 166 the SCM 120 disables the sensor PCBA 116 including CMOS image sensor 110 and optionally alerts the clinician that the sensor PCBA 116 has been disabled and/or should not be used.

In some embodiments, the predetermined time Δt is 120 minutes, or other suitable time.

According to some embodiments, the method 140 ensures that a single-use medical device including a sensor PCBA 116 can only be used on a single patient during a single procedure.

Figure 4:
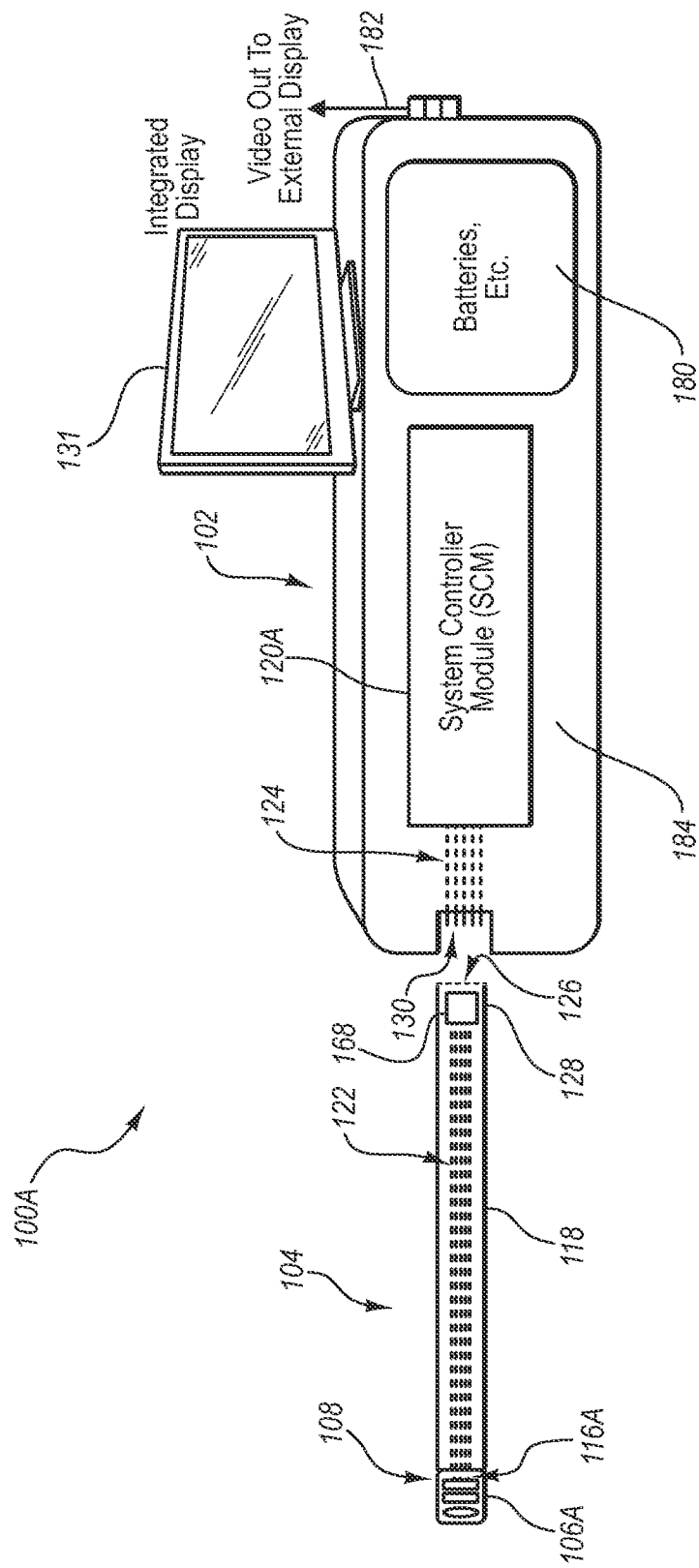
FIG. 4 includes a schematic diagram of an embodiment of a medical device that includes a reusable portion and a single use portion.

FIG. 4 includes a schematic diagram of an embodiment of a medical device 100A that includes a reusable portion 102 and a single use portion 104. The medical device 100A can be represented as an endoscopic device 100A that includes features of the endoscopic device 100 described above with respect to FIGS. 1-3 where like components are identified using like reference numbers.

In contrast to the endoscopic device 100 of FIG. 1, however, the endoscopic device 100A of FIG. 4 includes a disposable catheter 104A without an OTP chip 114 (FIG. 2). E.g., the camera and lens assembly 106A includes a sensor PCBA 116A that lacks an OTP chip 114. Additionally, the endoscopic device 100A includes an SCM module 120A which may or may not be configured similarly to the SCM 120 of FIGS. 1 and 2, the SCM module 120A generally providing control of the endoscopic device 100A.

Figure 5:
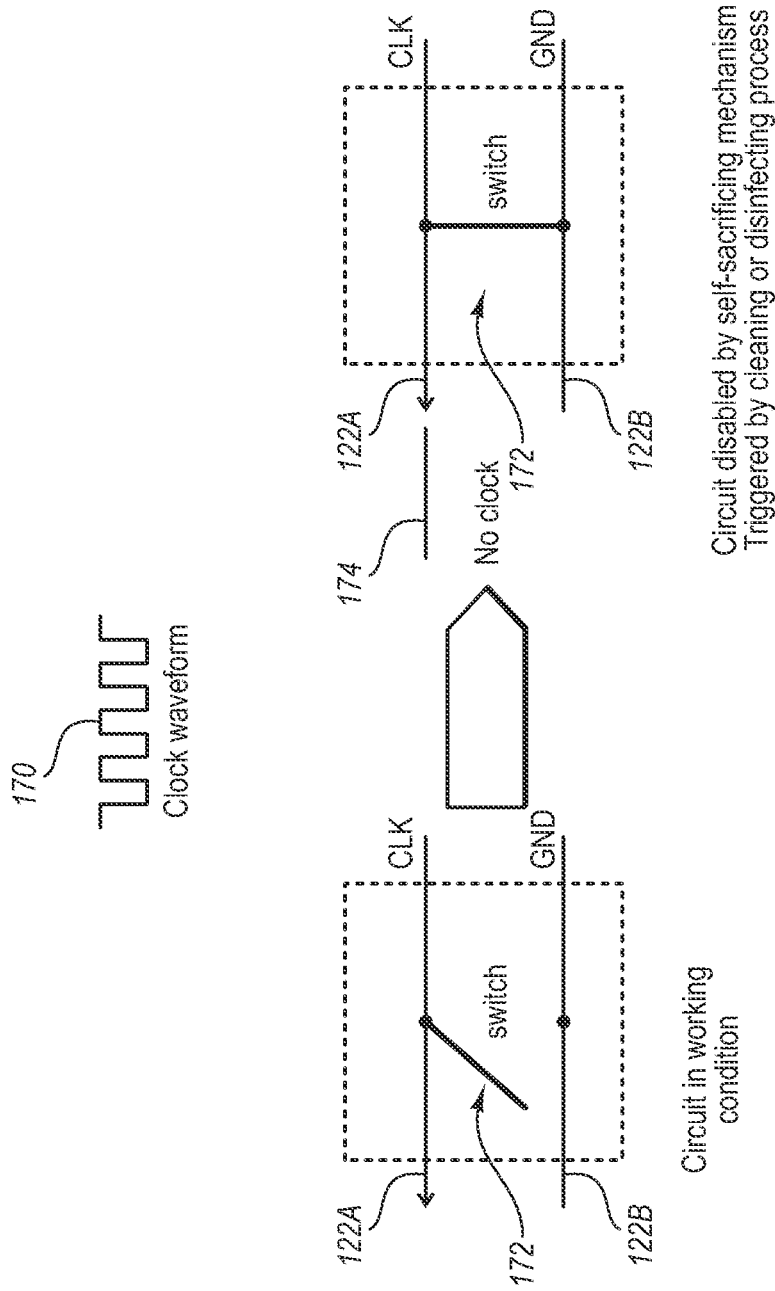
FIG. 5 includes a schematic diagram of an embodiment of a single use circuit that can be used in a single use portion of a medical device.

Furthermore, the endoscopic device 100A includes a self-sacrificing module (SSM) 168, rather than an OTP chip 114, for ensuring the disposable catheter 104 is not used more than once or on more than one patient. In this regard, and as shown in FIG. 5, the SCM 120A of the endoscopic device 100A is configured to supply a digital clock ("CLK") 170 to drive the components (e.g., a CMOS image sensor) of the PCBA 116A. So long as the digital clock 170 is provided to the components of the PCBA 116A, the components continue to function.

In some embodiments, the CLK signal 170 and/or a ground are provided over two of electrical lines 122 (FIG. 4), such as over a CLK line 122A and a ground ("GND") line 122B, to the PCBA 116A. The SSM 168 includes a switch 172 coupled between the CLK line 122A and GND line 122B. In normal operation, the switch 172 is open.

However, by closing the switch 172 or otherwise connecting the CLK line 122A to the GND line 122B, the CLK signal 170 is destroyed and a relative flat output 174 is created in place of the CLK signal 170. Without receiving the CLK signal 170, the components of the PCBA 116A are disabled.

Figure 6:
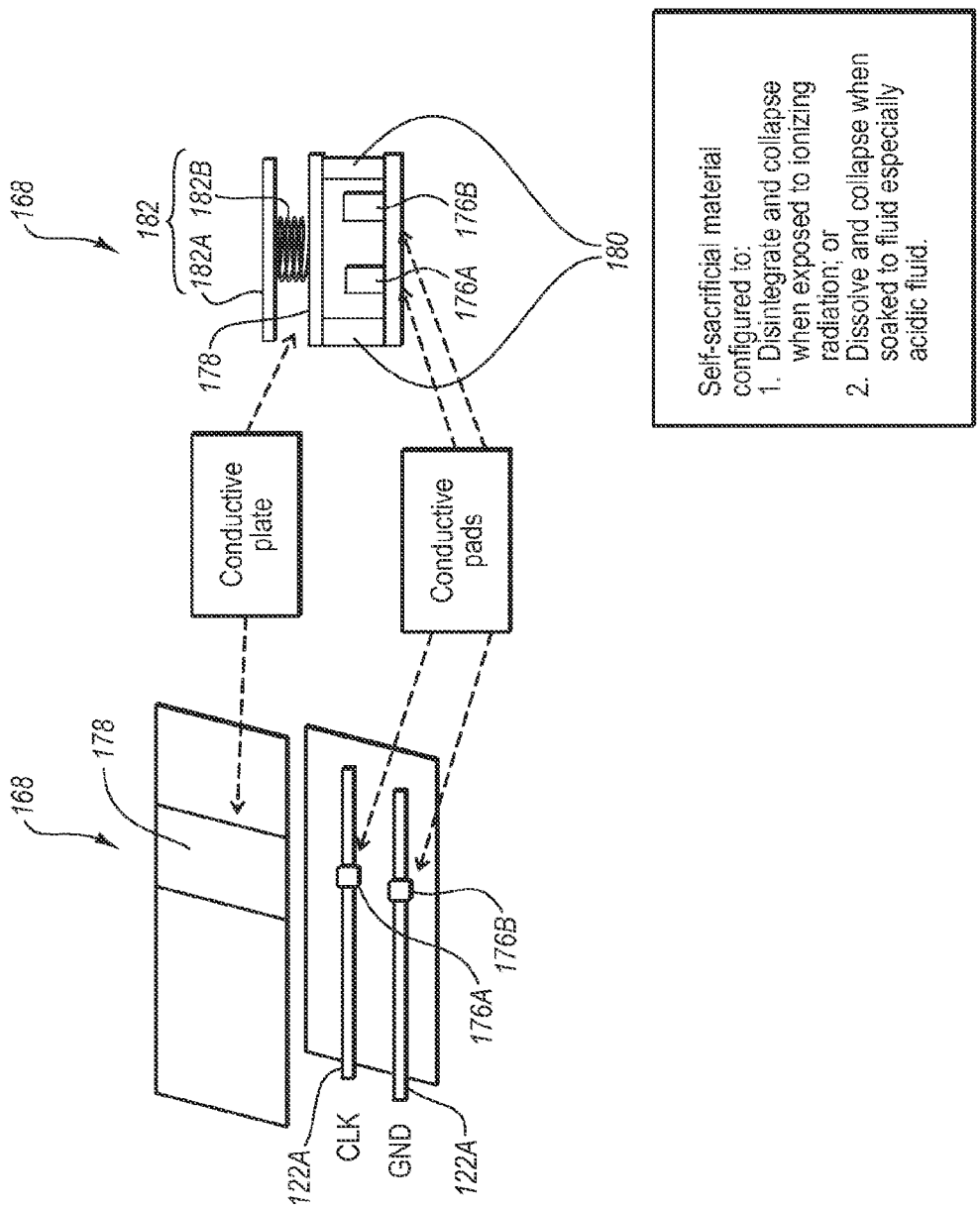
FIG. 6 includes a schematic diagram of an embodiment self-sacrificial component of a single use medical device.

FIG. 6 includes a schematic diagram of an embodiment self-sacrificial component 168 of a single use medical device. In particular, FIG. 6 discloses aspects of the SSM 168 module in more detail, the SSM 168 being configured to automatically close the switch 172 in response to the disposable catheter 104A of FIG. 4 being subjected to a sterilization procedure such as soaking in fluid or exposing to ionizing radiation. The left side of FIG. 6 is an exploded perspective view and the right side of FIG. 6 is a cross-sectional view of the SSM 168. As seen in FIG. 6, the SSM 168 includes a conductive pad 176A, 176B coupled to each of the CLK line 122A and GND line 122B. A conductive plate 178 is biased against sacrificial rods 180 towards conductive pads 176A, 176B by a biasing mechanism 182. The biasing mechanism 182 includes a base 182A and compressed spring 182B. The sacrificial rods 180 include a Teflon composite or other suitable material such that when soaked in fluid or exposed to ionizing radiation, the sacrificial rods 180 dissolve or disintegrate. Upon disintegration/dissolution of the sacrificial rods 180, the biasing mechanism 182 urges the conductive plate 178 against conductive pads 176A, 176B to close the circuit between the CLK line 122A and GND line 122B.

As shown in FIG. 6, the SSM 168 can be configured to disintegrate and collapse when exposed to ionizing radiation. Alternatively, the SSM can dissolve and collapse when soaked in a fluid, such as an acidic solution.

Figure 7:
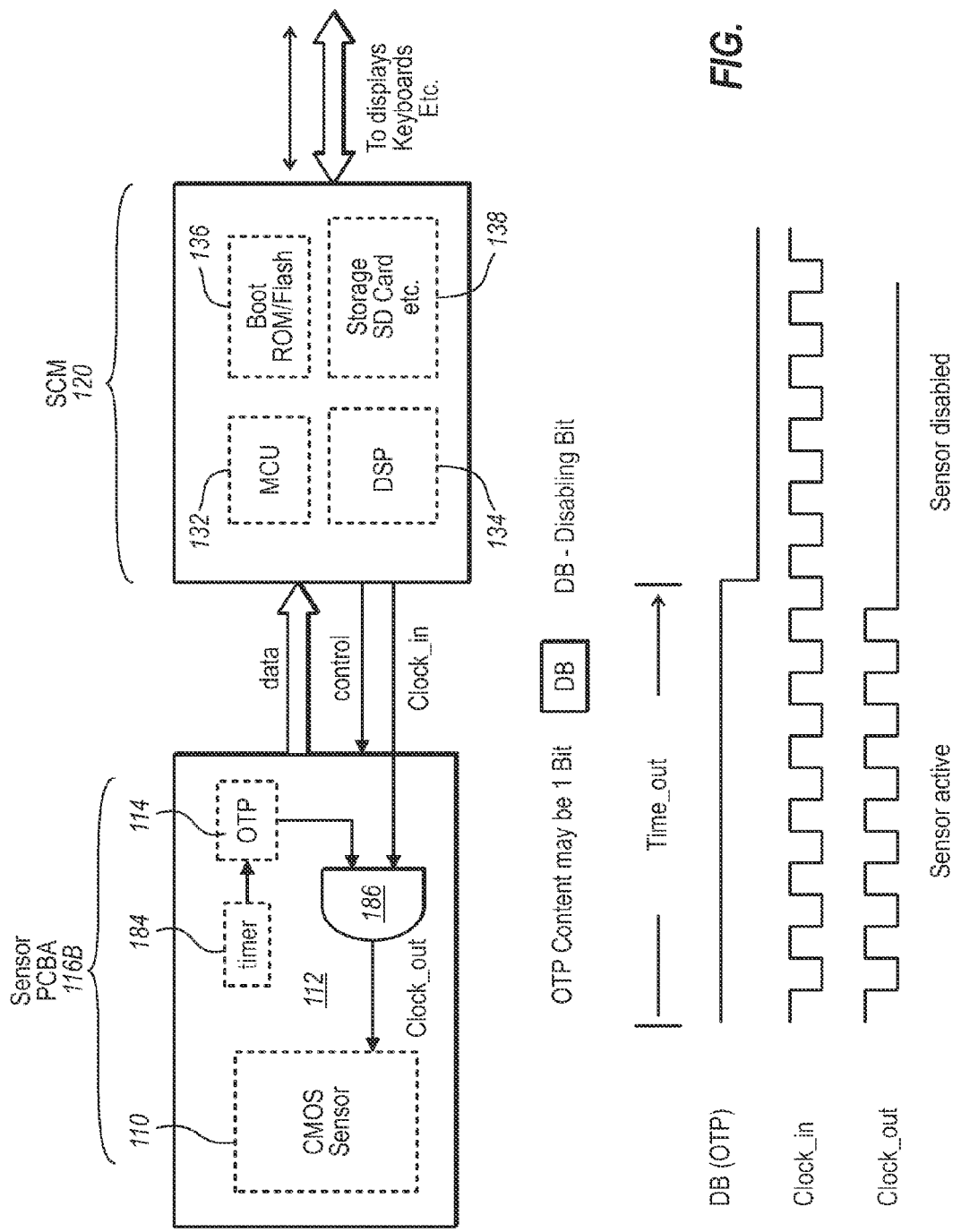
FIG. 7 includes a schematic diagram of an embodiment of a single use printed circuit board and corresponding signals.
Figure 8:
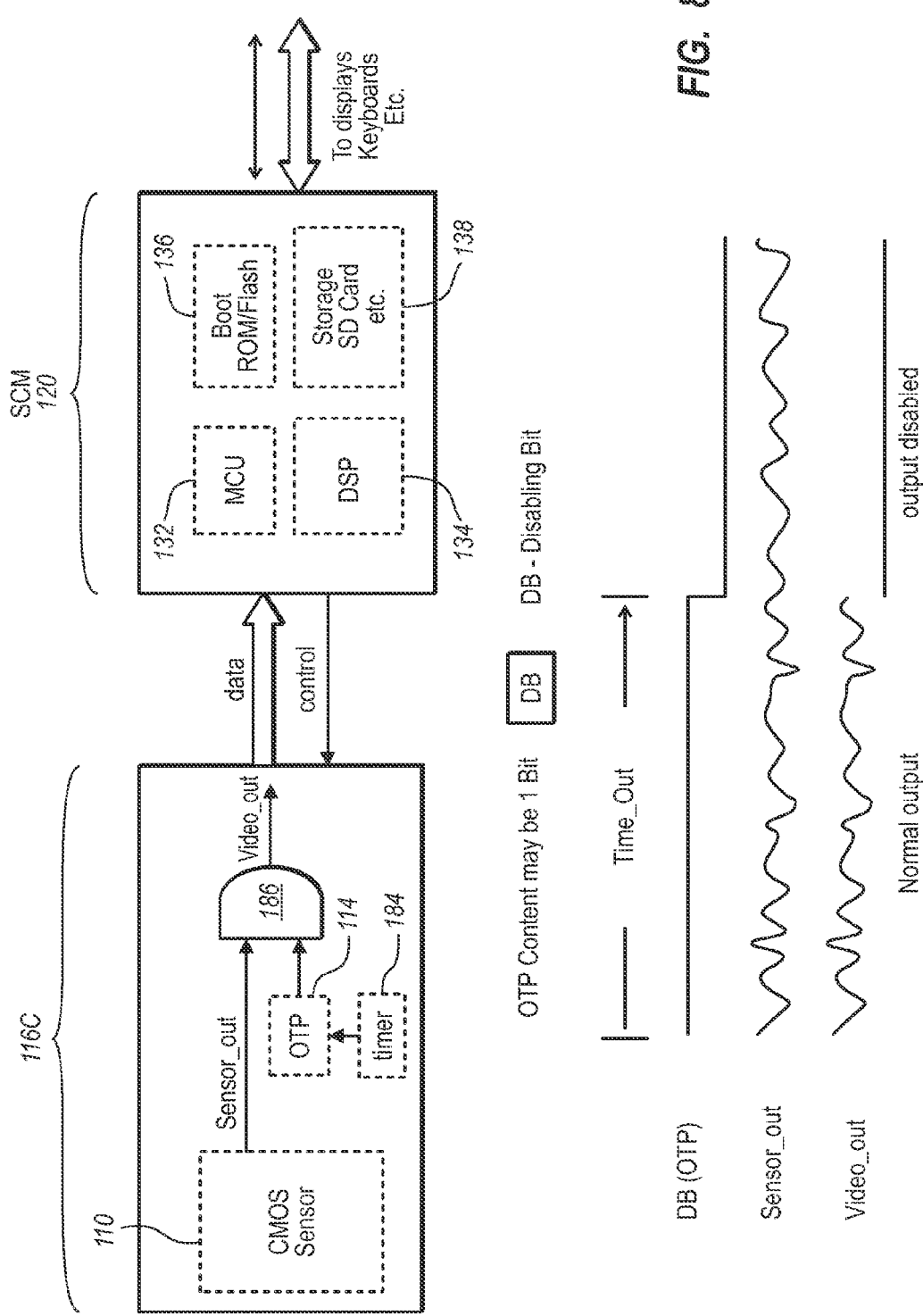
FIG. 8 includes a schematic diagram of another embodiment of a single use printed circuit board and corresponding signals.

In view of the foregoing, FIGS. 4, 5, and 6 describe and illustrate several different methods for disabling the CMOS sensor in a SUD 104. FIGS. 7 and 8 illustrate other examples of a sensor PCBA 116B, 116C that can be implemented in the disposable catheter 104 of FIG. 1 or other single-use medical devices according to some embodiments.

FIG. 7 includes a schematic diagram of an embodiment of a single use printed circuit board 116B and corresponding signals. In the example of FIG. 7, the sensor PCBA 116B includes the CMOS image sensor 110 and OTP chip 114 mounted on the PCB 112, and further includes a timer 184 and an AND circuit 186. The timer 114 is coupled to the OTP chip 114, and the OTP chip 114 is coupled to one of the inputs of the AND circuit 186. An input clock from the SCM 120 is coupled to the other input of the AND circuit 186. The output of the AND circuit 186 is coupled to the CMOS image sensor 110.

As shown in FIG. 7, one example of system operation in a procedure is described. In summary a catheter or SM is considered as used if its OTP is programmed (or "burned") longer than a preset Δt minutes ago. The Δt parameter can be adjusted by the manufacture and stored in the boot ROM for SCM controlled by the manufacture so it cannot be changed by software or other means during the operation.

Clinician open sterile package and get the single-use catheter and snap-on the Catheter to the Handle. The system is turned on by pushing power on button. The system will first boot up the SCM from boot ROM or FLASH. The clinician scans in or manually enters the Patient ID into the system. The system will automatically generate a Case ID (CID) from the Patient ID according to a predefined rules (stored in the ROM) such as a string truncated from the Patient ID string. CID and Patient ID should have a one-to-one relationship. At the same time, the SM module is initialized after SCM initialization. The system checks and reads the OTP from the CMOS, if the OTP has never been programmed, then it means this module has not been used. If it has been used, the OTP should contain a CID' and TS'. The (CID') from the OTP is compared to the CID generated from the Patient ID. If they are identical and the Time Stamp (TS') indicates that the OTP was programmed less than (Dt) minutes ago (for instance 60 minutes ago), then it is considered for the same patient in the same procedure. Upon completion of the procedure, the OTP DB bit will be burned to permanently disable the sensor.

In the cases either CID generated from the SCM does do not match the CID' or TS' indicates that OTP was programmed at least Δt minutes ago, the CMOS sensor will be disabled by a programming (burn) DB bit of the OTP. The SCM will alert the clinician that the Catheter or SM should not be used.

In the example of FIG. 8, the sensor PCBA 116C similarly includes the CMOS image sensor 110 and OTP chip 114 mounted on the PCB 112, and further includes timer 184 and AND circuit 186. The timer 184 is coupled to the OTP chip 114, and the OTP chip 114 is coupled to one of the inputs of the AND circuit 186. A sensor output from the CMOS image sensor 110 is coupled to the other input of the AND circuit 186. The output of the AND circuit 186 provides data output to the SCM 120.

In either of the examples of FIG. 7 or 8, the content of the OTP chip 114 may be one bit, e.g., a disabling bit ("DB"). The timer 184 is pre-programmed to run a predetermined length of time before programming the DB bit of the OTP chip 114. Once the DB bit of the OTP chip 114 is programmed (or pulled logically "low"), the Clock_out signal to the CMOS image sensor 110 is disabled in the example of FIG. 7, or the Video_out signal to the SCM 120 is disabled in the example of FIG. 8.

In the example of FIG. 7 or 8, and in operation, the timer 184 starts to run when a system including the sensor PCBA 116B, 116C is powered on. The time out (Time_Out) to trigger the OTP DB bit can be programmed according to various procedures. In some embodiments, sensor PCBAs 116B, 116C are color coded according to the corresponding Time_Out value. For instance, sensor PCBAs 116B, 116C may be green, blue or yellow for Time_Out values of 30 minutes, 60 minutes, or 90 minutes, respectively. The Time_Out of each sensor PCBA 116B, 116C is hard wired or preprogrammed and cannot be changed by the user.

According to some embodiments, the timer 184 memory is non-volatile. Thus, if a system including the sensor PCBA 116B, 116C is shut down or otherwise powered off, the elapsed time up to that point would be saved in non-volatile memory and when the system is powered back on, the timer 184 would continue its count from the value stored in the nonvolatile memory. For example, if the system is powered off after 15 minutes of being powered on and then powered back on at a later time, the timer will continue its count from 15 minutes up until reaching Time_Out.

Accordingly, FIGS. 1-8 disclose various schemes for disabling a disposable catheter 104 or other SUD including a CMOS image sensor to ensure it is only used a single time. The schemes disclosed herein are provided by way of example only and should not be construed to limit the invention. For instance, in some embodiments, after determining that a SUD including a CMOS image sensor has been used previously on a different patient, or during a different procedure, or the like, using an OTP chip or other suitable means, the SUD can be disabled by supplying a high voltage to the CMOS image sensor to thereby "fry" the CMOS image sensor. Particularly, for a SUD that normally uses a 3.3 volt power supply, the SUD could be disabled by switching the 3.3 volt power supply to a 30 volt power supply which would permanently disable the CMOS image sensor included in the SUD.

In one embodiment, a single use medical device can include a sensor module that is designed to be only capable of being used by having an OTP component on the SUD. In one aspect, a system controller can be designed to include the capability to program the OTP with a system time stamp and an ID generated from Patient ID. In one aspect, the system controller can be designed to reads a serial number of the electronics module in the SUD, such as a sensor PCBA, and the system controller can then tag it or embed the serial number into patient records. In one aspect, an algorithm can be used to detect and/or determine if an electronic module, such as a sensor PCBA, has been used and how long it has been used. In one aspect, the after a single used, the SUD is configured to shut down a sensor PCBA and disable it permanently so that the SUD is inoperable. In one aspect, a method to shut down a SUD that has a CMOS image sensor can include disabling the CMOS image sensor permanently using high voltage.

Figure 9:
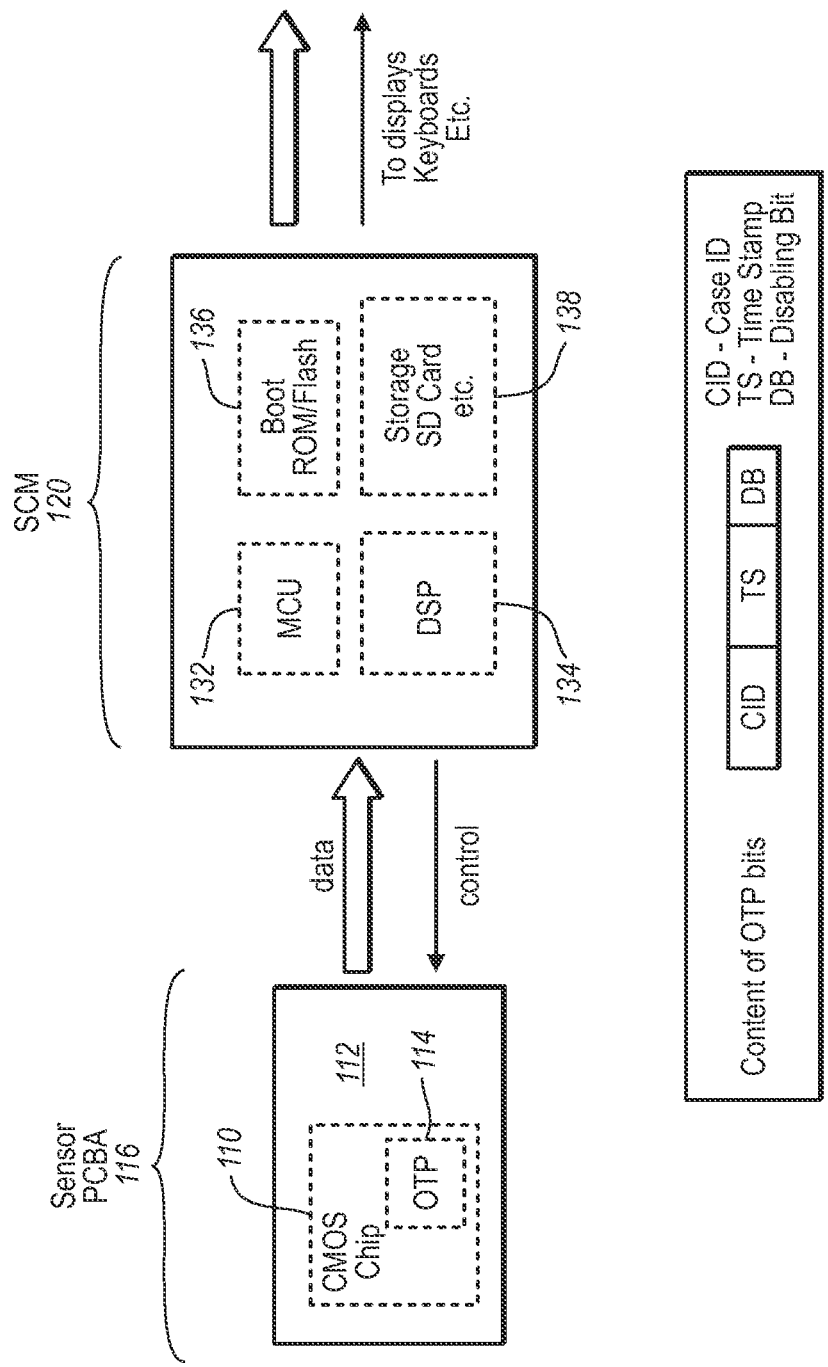
FIG. 9 includes a schematic diagram of another embodiment of electronic components of the medical device of FIG. 1, where the schematic diagram illustrates electronic components in the reusable portion and electronic components in the single use portion.

FIG. 9 includes a diagram of an embodiment of electronic components of the medical device of FIG. 1, where the schematic diagram illustrates electronic components in the reusable portion and electronic components in the single use portion. As shown, the SCM 120 includes a microcontroller unit ("MCU") 132 or other control module (e.g., controller, microcontroller, processor, microprocessor, or the like), a digital signal processor ("DSP") 134, a Boot read-only memory ("ROM") or flash memory 136, and/or a volatile or non-volatile storage device 138 such as an SD card. The sensor PCBA 116 includes a PCB 112 having a CMOS chip 110 that includes therewith an OTP chip 114. In general, the SCM 120 can write once to the OTP chip 114 and read multiple times from the OTP chip 114. Alternately or additionally, the SCM 120 reads and changes registers on the CMOS image sensor 110 to, for instance, disable the CMOS image sensor 110 by changing its registers.

In operation, at power on or reset, the SCM 120 boots from "boot code" stored in the Boot ROM/Flash 136. In some embodiments, the Boot ROM/Flash 136 also stores firmware for operating the endoscopic device 100 and implementing one or more of the methods described herein. Generally, the content in the Boot ROM/Flash 136 is read-only such that the content cannot be changed or modified by users of the endoscopic device 100.

With combined reference to FIGS. 1 and 9, the camera and lens assembly 108 includes a CMOS chip 110 mounted on a miniature printed circuit board ("PCB") 112 with one or more additional components such as passives. An OTP component 114 is embedded in the CMOS chip 110. The PCB 112 with CMOS chip 110 and one or more additional components are collectively referred to herein as a sensor PCB assembly ("sensor PCBA") 116. As disclosed at the bottom of FIG. 9, the content of the OTP component 114 may include one more bits representing, for instance, a time stamp ("TS") indicating a specific time when the disposable catheter 104 is first used, a patient case ID ("CID"), or the like. The TS and CID stored in the OTP component 114 uniquely associate the disposable catheter 104 with a time of first use and a patient.

According to some embodiments, the electrical lines 122, 124 between the sensor PCBA 116 and the SCM provide for a data path and a control path, including power supplies (VDD and VSS) to the sensor PCBA 116 and an LED, clock ("CLK"), single-ended analog output line and/or double-ended differential analog output lines. Optionally, control signals are shared among one or more of electrical lines 122, 124.

The CMOS chip 110 containing a OTP component 114, whether implemented in a disposable catheter 104 or other SUD, is configured to be permanently disabled after a single use to prevent the disposable catheter 104 or other SUD from being capable of being reused. As such, the sterilization process associated with many multiple-use devices and the risk of infection is substantially eliminated according to some embodiments. Moreover, the small size of the CMOS chip 110 facilitates truly minimally invasive procedures and real-time images suitable for use with diagnostic and surgical applications according to some embodiments.

Figure 10:
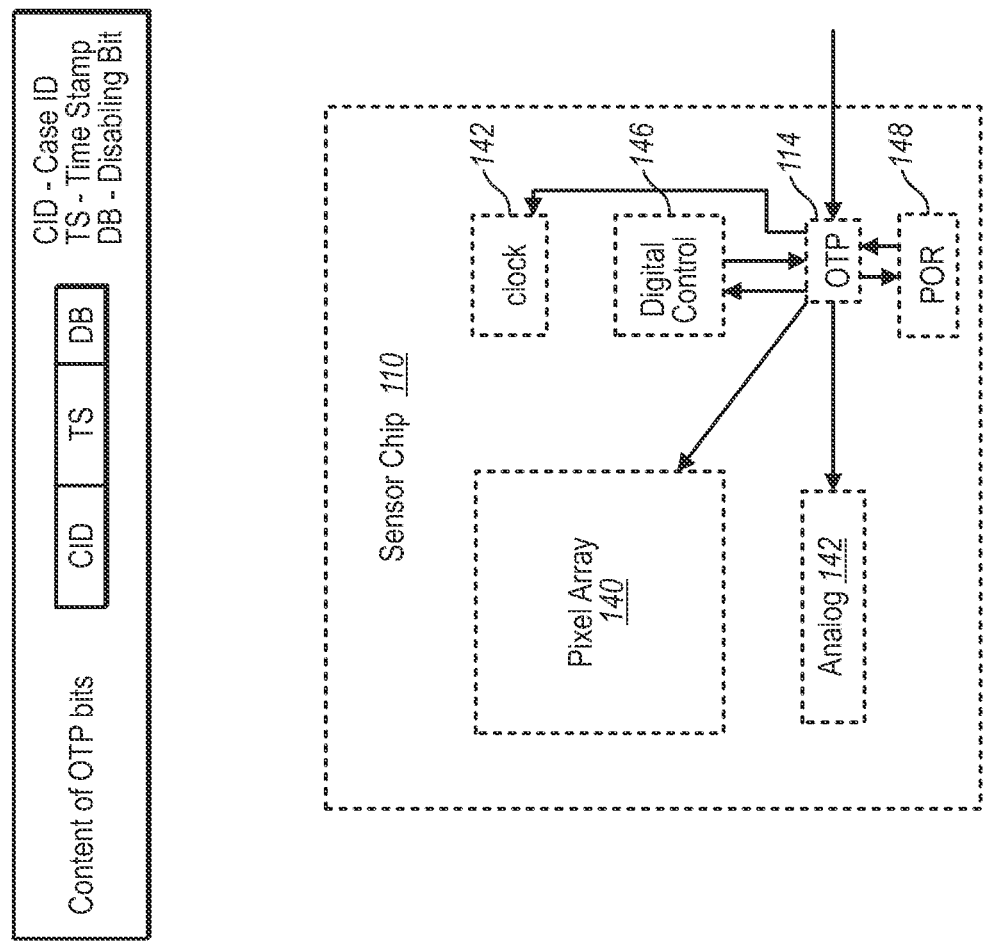
FIG. 10 includes a schematic diagram of an embodiment of a sensor chip having a OTP component and other components.

FIG. 10 illustrates an embodiment of computer processing for the CMOS chip 110 of FIG. 9, and additional details regarding an example embodiment of the CMOS chip 110 are disclosed. In the illustrated embodiment, the CMOS chip 110 includes the OTP component 114. Additionally, the CMOS chip 110 includes a pixel array 140, an analog block 142, clock 144, digital control 146, and power on reset ("POR") block 148.

The OTP component 114 can be one bit or multi-bit. The OTP bits content can be as shown. The OTP component 114 can control one or more of the components of the CMOS chip 110 as shown by the arrows. The OTP component 114 can be programmed by one or several or all of the various well known OTP chip programing, such as but not limited to a pin going off chip, digital logic, power-on-reset, or the like.

Figure 11:
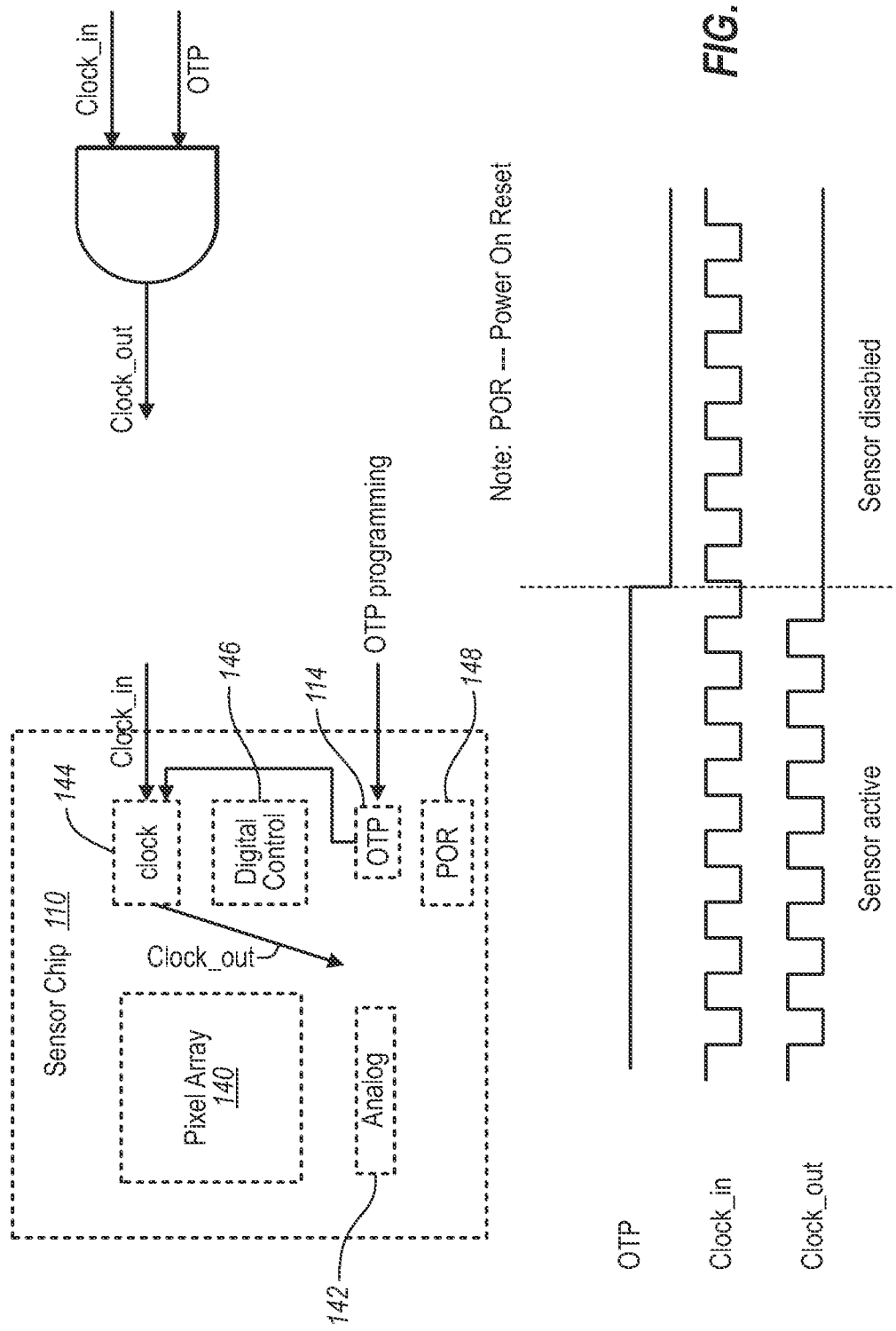
FIG. 11 includes a schematic diagram of an embodiment of a process for disabling the sensor chip of FIG. 10.
Figure 12:
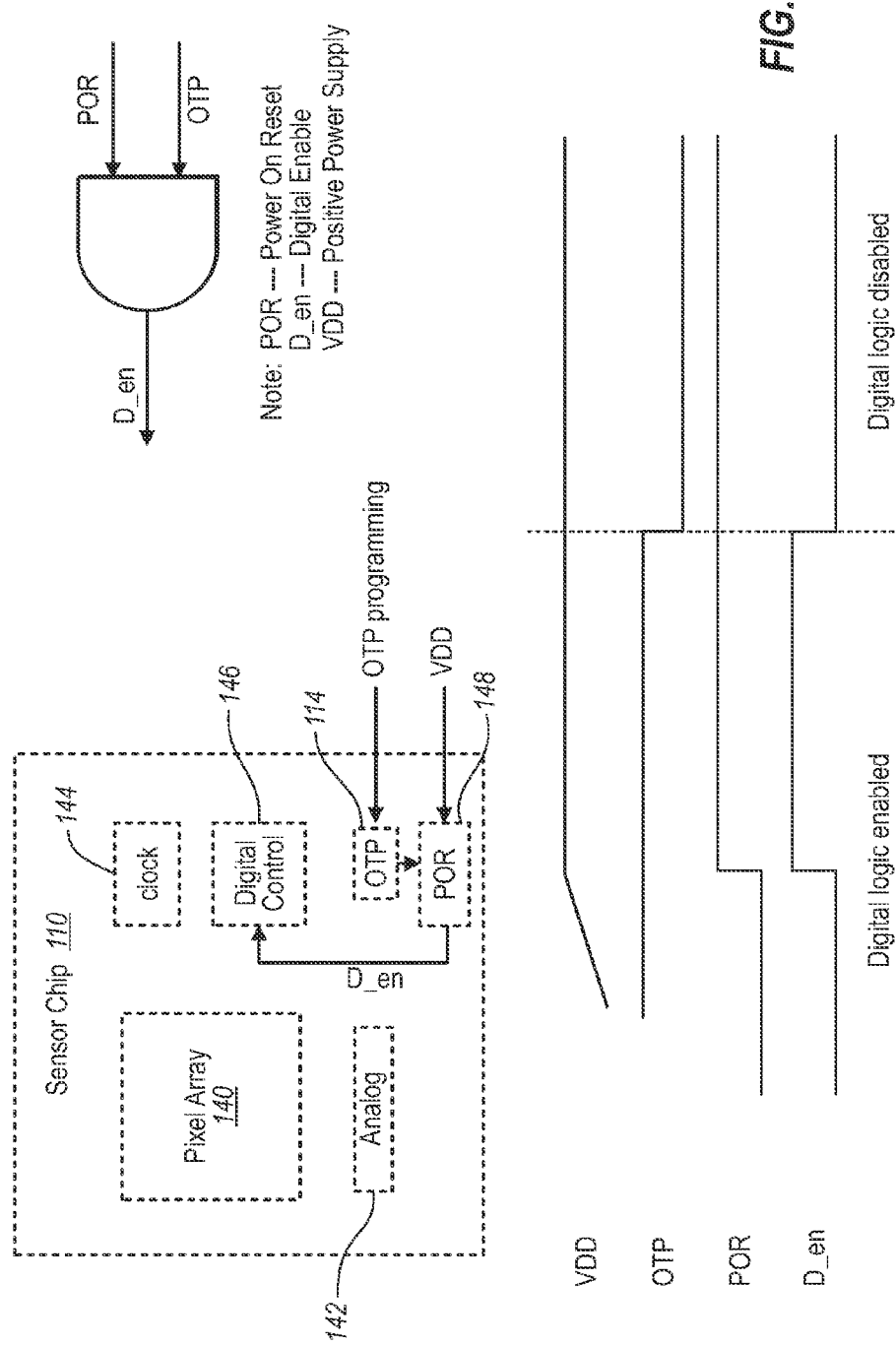
FIG. 12 includes a schematic diagram of an embodiment of a process for disabling the sensor chip of FIG. 10.
Figure 13:
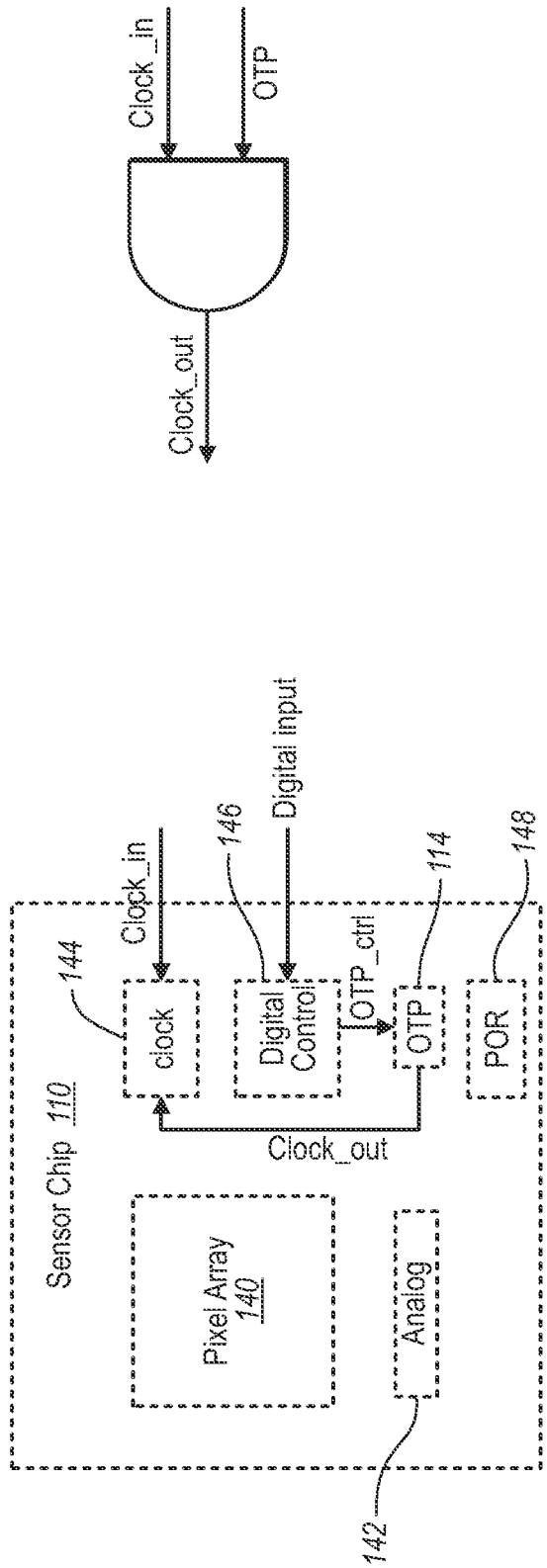
FIG. 13 includes a schematic diagram of an embodiment of a process for disabling the sensor chip of FIG. 10, arranged in accordance with at least one of the embodiments described herein, and which arrangement may be modified in accordance with the disclosure provided herein by one of ordinary skill in the art.

FIGS. 11, 12, and 13 disclose several different methods for disabling the CMOS chip 110 using the OTP component 114. In FIG. 11, for example, the output clock ("Clock_out") of the clock 144 depends on an input clock ("Clock_in") from the SCM 120 (FIGS. 1 and 9) and an output from the OTP component 114. After the disabling bit DB of the OTP component 114 is programmed, Clock_out is turned off and the CMOS chip 110 is permanently disabled.

In the example of FIG. 12, after the disabling bit DB of the OTP component 114 is programmed, a D_en signal is turned off and the CMOS chip 110 is permanently disabled. In both of FIGS. 11 and 12, the OTP component 114 is controlled from off-chip, e.g., from the SCM 120 (FIGS. 1 and 9).

In the example of FIG. 13, the OTP component 114 is programmed by digital control 146 in response to a particular digital input code. After the disabling bit DB of the OTP component 114 is programmed, Clock_out is turned off and the CMOS chip 110 is permanently disabled. For example, a particular pattern of digital input code can result in an OTP state change. If input code is "01100110" at serial input, the digital control logic will turn on OTP_ctrl bit, which results in OTP bit flip from 0 to 1, and disables the clock. Other similar bit flip protocols can be implemented.

With combined reference to FIGS. 1 and 9-13, one example of a method of a system operation to disable a medical device after a single use is disclosed. The method may be implemented by the endoscopic device 100, including disposable catheter 104 or other SUD device having, e.g., a CMOS chip 110 containing an OTP component 114. According to some embodiments, the method generally determines that a SUD component such as a disposable catheter 104 or other component including the CMOS chip 110 has already been used, and should therefore be disabled, if the OTP component 114 of the CMOS chip 110 has been programmed or burned more than a predetermined At minutes prior to checking the OTP component 114. Optionally, a parameter can be programmed by the manufacturer and stored in the boot ROM/Flash 136 of the SCM 120 to prevent the parameter from being changed by software or other means during operation.

In the discussion that follows, the method will be discussed in the context of a disposable catheter 104 including a CMOS chip 110 containing a OTP component 114 that can be implemented with the handle 102, with the understanding that the method can be applied using other components that include CMOS chips 110 containing OPT components 114 and/or that are implemented in devices other than the handle 102.

In some embodiments, the method begins after a clinician or other healthcare provider opens a sterile package containing a component such as a disposable catheter 104 or other component including a CMOS chip 110, and snaps the disposable catheter 104 onto the handle 102 via connectors 126, 130. The handle 102 is powered on, e.g., in response to the clinician pushing a power on button. The SCM 120 is booted from boot ROM/Flash 136. A Patient ID is obtained that corresponds to a patient on whom a medical procedure is to be performed using the endoscopic device 100. The Patient ID in some embodiments is obtained in response to the clinician scanning an electronic medical record ("EMR") corresponding to the patient or manually entering the Patient ID using an appropriate input device such as a keyboard connected to the handle 102.

The SCM 120 automatically generates a Case ID ("CID") corresponding to the Patient ID. The CID is generated according to predefined rules stored in, e.g., the boot ROM/Flash 136 in some examples. Optionally, the predefined rules specify truncating a string from a corresponding Patient ID string to generate the CID. In some embodiments, a one-to-one relationship exists between the Patient ID and the Case ID. Alternately or additionally, the method includes obtaining a time stamp ("TS") representing a current time.

In some embodiments, various other steps are executed after and/or simultaneously in association with the sensor PCBA 116. Specifically, the SCM 120 initializes the sensor PCBA 116 including the CMOS chip 110, and the SCM 120 checks the OTP component 114 from the CMOS chip 110 to then determine whether the OTP component 114 has ever been programmed. If the OTP component 114 has never been programmed, indicating that the CMOS chip 110 has never been used, the OTP component 114 is programmed with the CID and TS obtained.

On the other hand, if the SCM 120 determines that the OTP component 114 has previously been programmed, indicating that the CMOS chip 110 has been previously programmed, the previously programmed CID' and previously programmed TS' will already be stored in the OTP component 114 and are output by the OTP component 114. The CID obtained and generated from the Patient ID is compared to the previously programmed CID' output. If the CID and CID' are identical, then it is determined whether the OTP component 114 was programmed less than a predetermined time. Prior to checking the OTP component 114, the SCM 120 evaluates whether |TS−TS'|<Δt. In some embodiments, the value of Δt is 60 minutes, although the value of Δt may alternately be more or less than 60 minutes.

If it is determined that the CID and CID' are identical and if it is determined that the amount of time elapsed since the OTP component 114 was first programmed with TS' is less than the predetermined time Δt, the procedure continues until completion. After completion of the procedure, the disabling bit DB of the OTP component 114 is burned to permanently disable the CMOS chip 100.

Alternately, if it is determined that the CID and CID' are not identical, indicating that the patient on whom the CMOS chip 110 is being used is different than a patient on whom the CMOS chip 110 was used previously, or if it is determined that the amount of time elapsed since the OTP component 114 was first programmed with TS' is at least the predetermined time Δt, then the CMOS chip 110 is disabled by a programming (burn) of the disabling bit DB of the OTP 114. Optionally, the clinician is alerted that the disposable catheter 104 and/or CMOS chip 110 have been disabled and/or should not be used.

In some embodiments, the predetermined time Δt is 120 minutes, or other suitable time.

According to some embodiments, the method ensures that a single-use medical device including a CMOS chip 110 containing a OPT component 114 can only be used on a single patient during a single procedure.

Accordingly, a disposable medical device module can be prepared that has an embedded OTP component on it for single use application. The module can include a system controller designed to program the OTP with one or more of the following: with system time stamp; with an ID generated from Patient ID; and a dedicated control signal. The module can include a system controller designed to read the serial number of the electronics module such as a sensor PCBA and ability to tag it or embedded into patient records. The module can include an algorithm configured to detect and/or determine if an electronic module such as a CMOS chip has been used during a procedure. Various methods can be used to disable the CMOS chip, such as by disabling the clock (CLK) to the CMOS chip using the embedded OTP component, disabling the digital enabling D_en inside the CMOS chip, changing the state of the OTP component by "self-destroy" codes, or the like The endoscopic device can include a handle and a disposable component that is removably attachable to the handle. The disposable component can include a CMOS chip with an embedded one-time programmable chip. A method of operating the endoscopic device to prevent multiple uses of the disposable component can include: generating a first unique case identifier corresponding to a first unique patient identifier of a patient undergoing a medical procedure; obtaining a first time stamp representing a current time; determining that the one-time programmable chip has previously been programmed with a second unique case identifier and a second time stamp; when the first unique case identifier is different than the second unique case identifier, or when the amount of time elapsed from an initial time represented by the second time stamp to a subsequent time represented by the first time stamp is greater than a predetermined amount of time, disabling the CMOS chip by programming a disabling bit on the one-time programmable chip.

In one embodiment, the disabling bit on the onetime programmable chip disables a clock (CLK) required for operation by the CMOS chip. Optionally, programming the disabling bit on the one-time programmable chip disables a digital enabling D_en signal within the CMOS chip. In one aspect, the disabling bit on the one-time programmable chip is programmed in response to receiving a "self-destroy" code within the CMOS chip.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is also to be understood that the terminology used herein is for the purpose of describing particular embodiments only, and is not intended to be limiting.

In an illustrative embodiment, any of the operations, processes, etc. described herein can be implemented as computer-readable instructions stored on a computer-readable medium. The computer-readable instructions can be executed by a processor of a mobile unit, a network element, and/or any other computing device.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those generally found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

Figure 14:
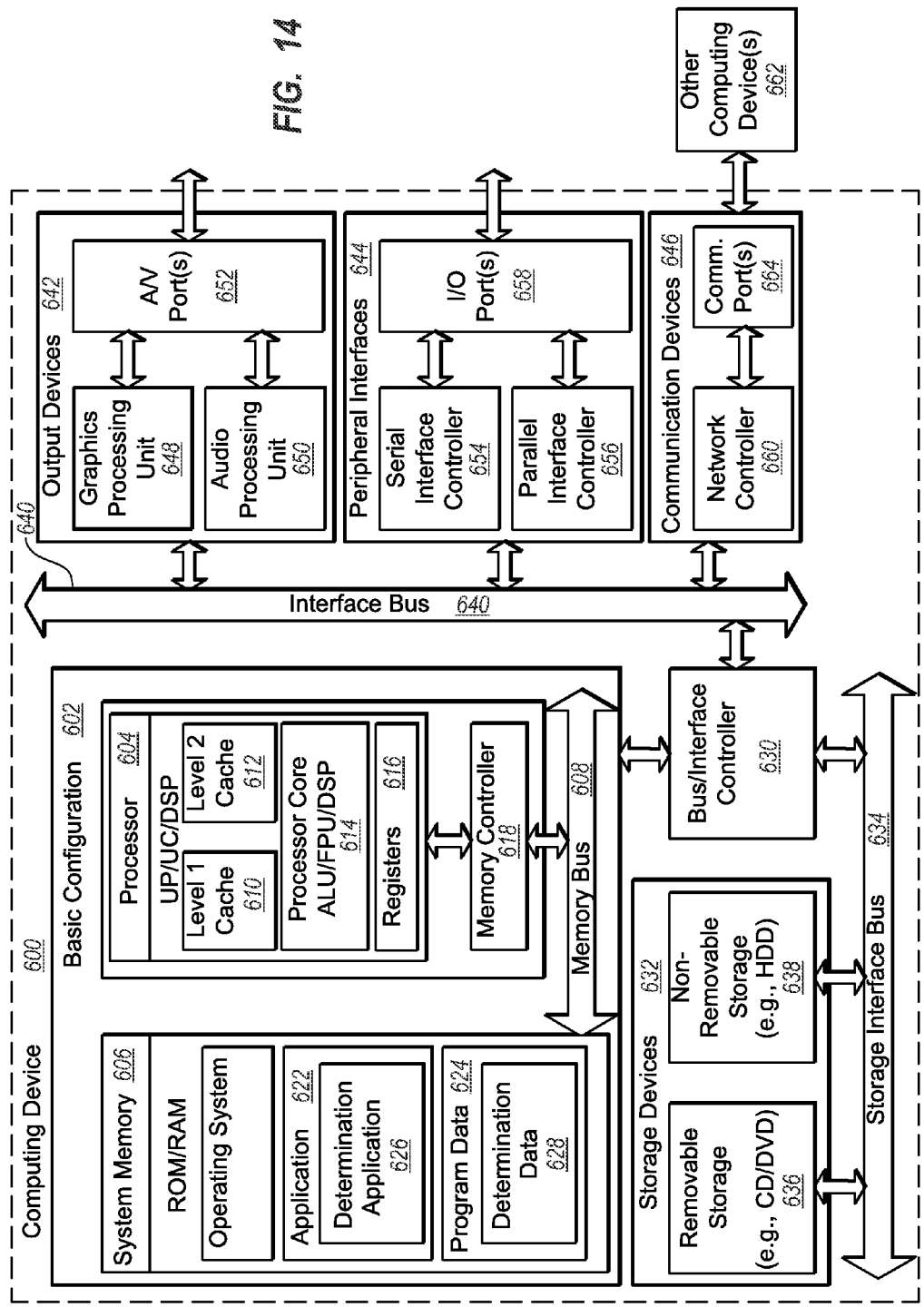

FIG. 14 shows an example computing device 600 that is arranged to perform any of the computing methods described herein. The computing system 600 can represent a user side computing device, such as a reusable portion of a medical device or a single use portion of a medical device. The components of the computing system 600 can be included in the single use portion of the medical device to facilitate a computing method that disables the single use portion or single use medical device. In a very basic configuration 602, computing device 600 generally includes one or more processors 604 and a system memory 606. A memory bus 608 may be used for communicating between processor 604 and system memory 606.

Depending on the desired configuration, processor 604 may be of any type including but not limited to a microprocessor (μP), a microcontroller (μC), a digital signal processor (DSP), or any combination thereof. Processor 604 may include one more levels of caching, such as a level one cache 610 and a level two cache 612, a processor core 614, and registers 616. An example processor core 614 may include an arithmetic logic unit (ALU), a floating point unit (FPU), a digital signal processing core (DSP Core), or any combination thereof. An example memory controller 618 may also be used with processor 604, or in some implementations memory controller 618 may be an internal part of processor 604.

Depending on the desired configuration, system memory 606 may be of any type including but not limited to volatile memory (such as RAM), non-volatile memory (such as ROM, flash memory, etc.) or any combination thereof. System memory 606 may include an operating system 620, one or more applications 622, and program data 624. Application 622 may include a determination application 626 that is arranged to perform the functions as described herein including those described with respect to methods described herein. Program Data 624 may include determination information 628 that may be useful for analyzing the contamination characteristics provided by the sensor unit 240. In some embodiments, application 622 may be arranged to operate with program data 624 on an operating system 620 such that the work performed by untrusted computing nodes can be verified as described herein. This described basic configuration 602 is illustrated in FIG. 6 by those components within the inner dashed line.

Computing device 600 may have additional features or functionality, and additional interfaces to facilitate communications between basic configuration 602 and any required devices and interfaces. For example, a bus/interface controller 630 may be used to facilitate communications between basic configuration 602 and one or more data storage devices 632 via a storage interface bus 634. Data storage devices 632 may be removable storage devices 636, non-removable storage devices 638, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 606, removable storage devices 636 and non-removable storage devices 638 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 600. Any such computer storage media may be part of computing device 600.

Computing device 600 may also include an interface bus 640 for facilitating communication from various interface devices (e.g., output devices 642, peripheral interfaces 644, and communication devices 646) to basic configuration 602 via bus/interface controller 630. Example output devices 642 include a graphics processing unit 648 and an audio processing unit 650, which may be configured to communicate to various external devices such as a display or speakers via one or more A/V ports 652. Example peripheral interfaces 644 include a serial interface controller 654 or a parallel interface controller 656, which may be configured to communicate with external devices such as input devices (e.g., keyboard, mouse, pen, voice input device, touch input device, etc.) or other peripheral devices (e.g., printer, scanner, etc.) via one or more I/O ports 658. An example communication device 646 includes a network controller 660, which may be arranged to facilitate communications with one or more other computing devices 662 over a network communication link via one or more communication ports 664.

The network communication link may be one example of a communication media. Communication media may generally be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 600 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 600 may also be implemented as a personal computer including both laptop computer and non-laptop computer configurations.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims. All references recited herein are incorporated herein by specific reference in their entirety.

The invention claimed is:

1. A single use medical device comprising:
a single use medical device module configured for use within a body of a subject receiving a medical procedure, the single use medical device module comprising:
an electronic component having a one-time programmable ("OTP") component that is configured to render the single use medical device module unusable after being used in the medical procedure in the subject.

2. The single use medical device of claim 1, wherein the electronic component includes an image sensor.

3. The single use medical device of claim 1, wherein the OTP component is operably coupled with the electronic component.

4. The single use medical device of claim 1, wherein the OTP component is contained within the electronic component.

5. The single use medical device of claim 2, wherein the electronic component is configured as a CMOS image sensor.

6. The single use medical device of claim 1, wherein the OTP component is configured to operate one time, and thereafter it does not allow the single use medical device to operate.

7. The single use medical device of claim 1, wherein the OTP component includes a self-sacrificing module (SSM) that self-destructs after being used one time.

8. The single use medical device of claim 1, wherein the OTP component is operably coupled with a timer and an AND circuit, when the timer reaches a certain time, the single use medical device no longer works.

9. The single use medical device of claim 1, wherein the OTP component includes a disabling bit (DB) circuit that is programmed to disable the single use medical device when a Clock_out signal is received by the DB circuit.

10. The single use medical device of claim 1, wherein the OTP component is configured to control various electronic components of the medical device within the single use medical device module.

11. The single use medical device of claim 1, wherein the OTP component is configured to be programmed one time by various electronic components of the medical device within the single use medical device module.

12. The single use medical device of claim 1, wherein the OTP component is configured such that a state change of a signal to the OTP component disables the single use medical device module.

13. The single use medical device of claim 1, comprising a controller configured to program the OTP with system time stamp and an ID generated from Patient ID.

14. The single use medical device of claim 1, comprising a controller configured to read the serial number of one or more electronics modules of the single use medical device module.

15. The single use medical device of claim 1, comprising a controller configured to tag a serial number of one or more electronics modules of the single use medical device module, and associate the serial number with a Patient ID.

16. The single use medical device of claim 1, wherein the electronic component having the OTP component includes an algorithm that is processed in order to render the single use medical device module unusable after being used in the medical procedure in the subject.

17. The single use medical device of claim 1, wherein the algorithm is configured to process data in order to detect and/or determine if the OTP component has been programmed.

18. The single use medical device of claim 1, wherein the single use medical device module is configured to disable an image sensor by one or more of the following:
   disabling a clock (CLK) to a chip of the image sensor, the chip being operably coupled with the OTP component;
   disabling a digital enabling Den inside the image sensor; or
   changing a state of the OTP component with "self-destroy" codes.

19. A medical device comprising:
   a reusable portion; and
   a single use portion comprising the single use medical device of claim 1.

20. In a medical device system comprising a reusable medical device and the single use medical device of claim 1, with the reusable medical device removably receiving the single use medical device, a method of operating the single use medical device, the method comprising:
   using the single use medical device;
   programming the OTP component; and
   terminating use of the single use medical device.

21. The method of claim 20, further comprising:
   attempting to reuse the single use medical device, the single use medical device being unusable.

22. The method of claim 20, further comprising:
   the single use medical device providing an indication that the single use medical device has already been used or that the single use medical device is not operational.

23. The method of claim 20, further comprising:
   generating a first unique case identifier corresponding to a first unique patient undergoing a medical procedure;
   obtaining a first time stamp representing a current time; and
      determining that the OTP component has previously been programmed with a second unique case identifier and a second time stamp, when the first unique case identifier is different than the second unique case identifier, or when the amount of time elapsed from an initial time represented by the second time stamp to a subsequent time represented by the first time stamp is greater than a predetermined amount of time, disabling the single use medical device module by programming a disabling bit on the one-time programmable chip; or
      determining that the OTP component has not been previously programmed, wherein the single use medical device module is operational.

* * * * *